(12) United States Patent
Kalinka et al.

(10) Patent No.: US 7,626,724 B2
(45) Date of Patent: Dec. 1, 2009

(54) AUTO-TRACKING SPECTROPHOTOMETER

(75) Inventors: Gary T. Kalinka, Wyoming, MI (US); Timothy L. Walker, West Olive, MI (US); Frederick G. Robinson, Hamilton, MI (US); Bernard J. Berg, Wayland, MI (US); Douglas V. Baker, Middleville, MI (US)

(73) Assignee: X-Rite, Inc., Grand Rapids, MI (US)

( * ) Notice: Subject to any disclaimer, the term of this patent is extended or adjusted under 35 U.S.C. 154(b) by 978 days.

(21) Appl. No.: 11/122,638

(22) Filed: May 5, 2005

(65) Prior Publication Data

US 2005/0254074 A1    Nov. 17, 2005

Related U.S. Application Data

(60) Provisional application No. 60/568,356, filed on May 5, 2004.

(51) Int. Cl.
*H04N 1/40*    (2006.01)
*H04N 1/46*    (2006.01)

(52) U.S. Cl. .................. 358/1.9; 358/3.24; 358/504

(58) Field of Classification Search ............ 358/402, 358/406, 487, 488, 500, 504, 505, 506, 518, 358/530, 3.24; 382/162, 167; 356/73, 404, 356/406, 418, 425, 402
See application file for complete search history.

(56) References Cited

U.S. PATENT DOCUMENTS

| | | | |
|---|---|---|---|
| 3,960,451 A | 6/1976 | Wirz et al. | |
| 4,003,660 A | 1/1977 | Christie, Jr. et al. | |
| 4,231,564 A * | 11/1980 | Miyagawa et al. | 271/95 |
| 4,494,875 A | 1/1985 | Schramm et al. | |
| 4,565,450 A | 1/1986 | Wirz et al. | |
| 4,907,036 A | 3/1990 | Morita | |
| 4,990,793 A | 2/1991 | Bonigk et al. | |
| 5,073,028 A | 12/1991 | Bowden et al. | |
| 5,446,559 A * | 8/1995 | Birk | 358/473 |
| 5,701,175 A | 12/1997 | Kostizak et al. | |
| 6,028,682 A * | 2/2000 | Ott et al. | 358/497 |
| 6,031,617 A * | 2/2000 | Berg et al. | 356/402 |
| 6,100,982 A * | 8/2000 | Tobias et al. | 356/617 |
| 6,215,552 B1 * | 4/2001 | Acquaviva et al. | 356/601 |
| 6,690,471 B2 * | 2/2004 | Tandon et al. | 356/420 |
| 6,697,106 B1 * | 2/2004 | Saito | 348/222.1 |
| 6,765,674 B2 | 7/2004 | Orelli et al. | |

FOREIGN PATENT DOCUMENTS

| | | |
|---|---|---|
| DE | 3144643 | 5/1983 |
| DE | 3220300 | 8/1983 |
| DE | 3414573 | 10/1985 |
| DE | 3440706 | 5/1986 |
| DE | 3614092 | 10/1987 |

(Continued)

*Primary Examiner*—James A Thompson
(74) *Attorney, Agent, or Firm*—McCarter & English, LLP

(57) ABSTRACT

An auto-tracking spectrophotometer has a moveable look-ahead sensor for scanning at least a portion of a color matrix. The look-ahead sensor finds a portion of the color matrix for measurement by an optical system. The optical system for measuring the color matrix is then guided using the information provided by the look-ahead sensor.

25 Claims, 6 Drawing Sheets

FOREIGN PATENT DOCUMENTS

| | | |
|---|---|---|
| DE | 3708652 | 9/1988 |
| DE | 4013421 | 10/1991 |
| DE | 4013422 | 10/1991 |
| DE | 4104537 | 8/1992 |
| EP | 0062787 | 10/1982 |
| EP | 0108889 | 5/1984 |
| GB | 2043883 | 10/1980 |
| GB | 2167712 | 6/1986 |
| WO | WO-1996/08703 | 3/1996 |
| WO | WO-2001/57485 | 8/2001 |

\* cited by examiner

AUTO-TRACKING SPECTROPHOTOMETER

This patent application claims the benefit of Provisional Patent Application No. 60/568,356, filed May 5, 2004, and entitled AUTO-TRACKING SPECTROPHOTOMETER.

BACKGROUND OF THE INVENTION

An auto-tracking spectrophotometer (ATS) measures and analyzes spectral data. Since spectral data provides the most complete and accurate description of color, an ATS is the ideal control system for both process and special color print jobs.

An ATS has a table for holding a color composition, a head for performing a scan of the color matrix, and a station, located at one end of the table. In order to use the ATS, an operator places a color graphic composition have a color target on the ATS platen. A vacuum pump is then energized so as to hold the composition onto the table.

The ATS head then scans the entire color target first to locate the beginning and ending points of the color target. After the beginning and ending of the color target are located, the ATS assumes that the color bar proceeds linearly between the beginning and ending of the color bar. Based upon this assumption, the ATS positions its data acquisition optics over what should be the color target, and then scans the area. After the head returns to the station, the measurement is then transmitted to a computer. Software on the computer displays an overview of the color data. The computer or an operator may then adjust the controls of a press used to more accurately reproduce the graphic composition.

ATS have proven invaluable in modern printing plants. However, they have limitations. Care must be taken by the operator of the ATS to align composition in the ATS. If not, the color target may be slightly curved when placed on the table. Further, if the composition is contained on a folded sheet of paper, additional care must be taken to compensate for the fold in the color target. If the color target is not properly aligned, the color target may not be accurately read.

Additionally, at least two scans are required by the ATS. The multiple scans may cause significant time delays. Finally, even with the multiple scans, the alignment of the color target may not be acceptable, resulting in faulty color information.

Further, the scan information is not transmitted to the computer until the head is returned to the station. This delays the time before the data is analyzed, resulting in delays in completing the print job.

An improved ATS which overcomes these problems is thus highly desirable.

SUMMARY OF THE INVENTION

An improved ATS is provided with a look-ahead visual sensor. The look-ahead sensor retrieves an image and a tracking controller finds the location of a color matrix. The color matrix could be a color target, a color profile target, a color bar code, a color picture, or any other amalgamation of colors. A controller moves the data acquisition optics in response to output from the look-ahead sensor. In this way, the data acquisition optics maintains a proper orientation with respect to the color matrix.

Additionally, a stepper motor for controlling movement of the ATS head in an X-direction is controlled directly by the head. Thus, all components for accurately tracking the color bar are located in the head.

In order to improve the efficiency of the ATS, the vacuum pump is provided with a solenoid controlling the coupling of vacuum holes located in the paper table with the vacuum pump.

During the scan, information from the data acquisition optics is continually transmitted to a remote computer by way of a communication channel between the head and the computer. Thus, the computer can immediately begin analyzing the data.

The communication channel is established by way of a communication interface, which could be an Ethernet connection. The head communicates to the by way of an Ethernet connection.

These and other objects, advantages and features of the invention will be more readily understood and appreciated by reference to the detailed description of the drawings.

DETAILED DESCRIPTION OF THE DRAWINGS

Figure 1:
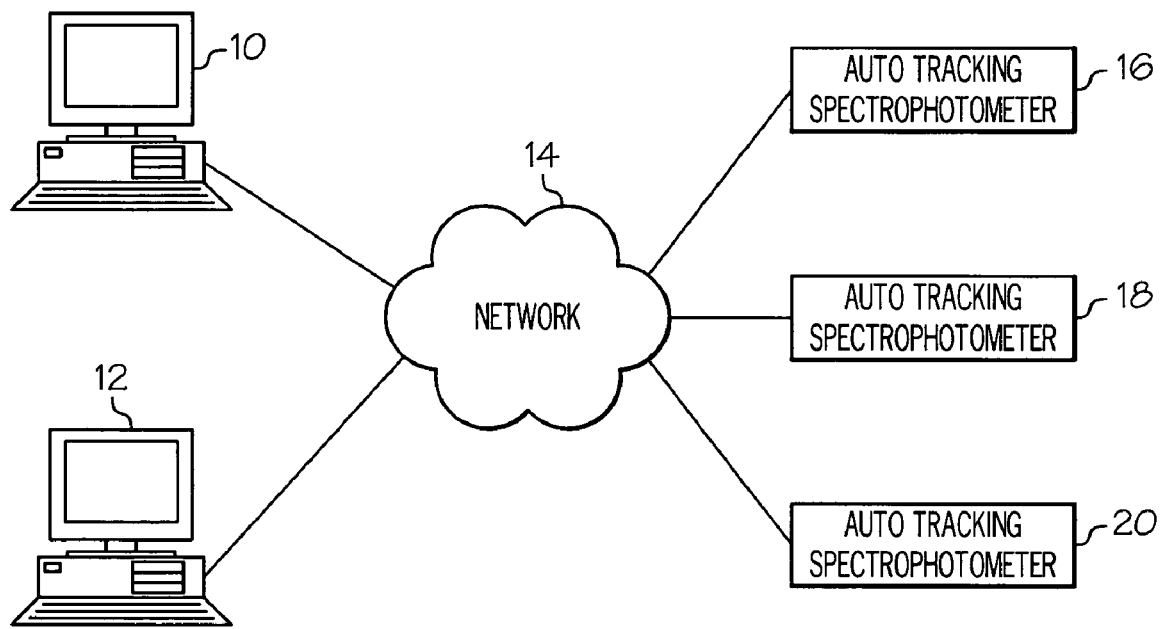
FIG. 1 shows several auto-tracking spectrophotometers connected to computers by way of a network.

FIG. 1 shows a printing plant with several ATS. Computers 10, 12 are connected by way of network 14 to a plurality of ATS systems 16, 18, 20. ATS systems 16, 18, 20 may communicate with computers 10, 12 by way of a standard protocol such as TCP/IP, or, if necessary, by a proprietary communication protocol.

Figure 2:
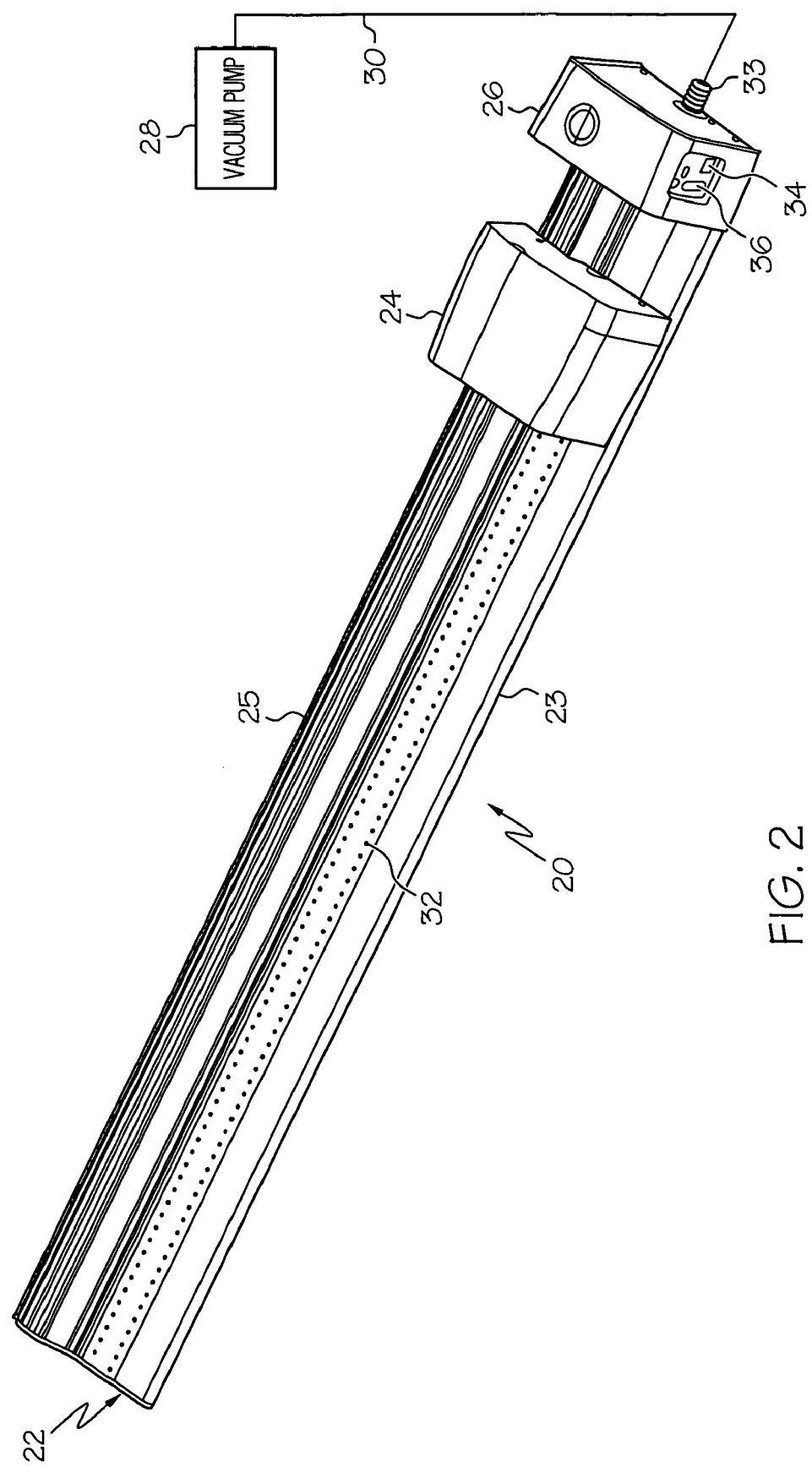
FIG. 2 shows an auto-tracking spectrophotometer.

FIG. 2 shows an ATS 20. ATS 20 consists of table 22, head 24, and station 26. Table 22 includes platen 23 and track 25. Table 22 is sample holding surface. In some applications, table 22 could be a curved surface.

Vacuum pump 28 is attached to station 26 by way of tube 30 and vacuum inlet 33. Table 22 has vacuum holes 32. When a graphic composition is placed on table 22, vacuum pump 28 is energized, thus creating a means to hold the graphic composition to table 22. The graphic composition is generally on a substrate, such as paper.

Station 26 includes communication interface 34 and RS232 interface 36. ATS 20 can be connected to a network by way of network interface 34. Network interface 34 could be a standard RJ-45 connection. ATS 20 could be directly connected to a computer by way of RS232 interface 36 or network interface 34.

After a graphic composition is placed on platen 23, head 24 moves across the color chart and reads the color chart on the graphic composition, and transmits the information to a computer.

Figure 3:
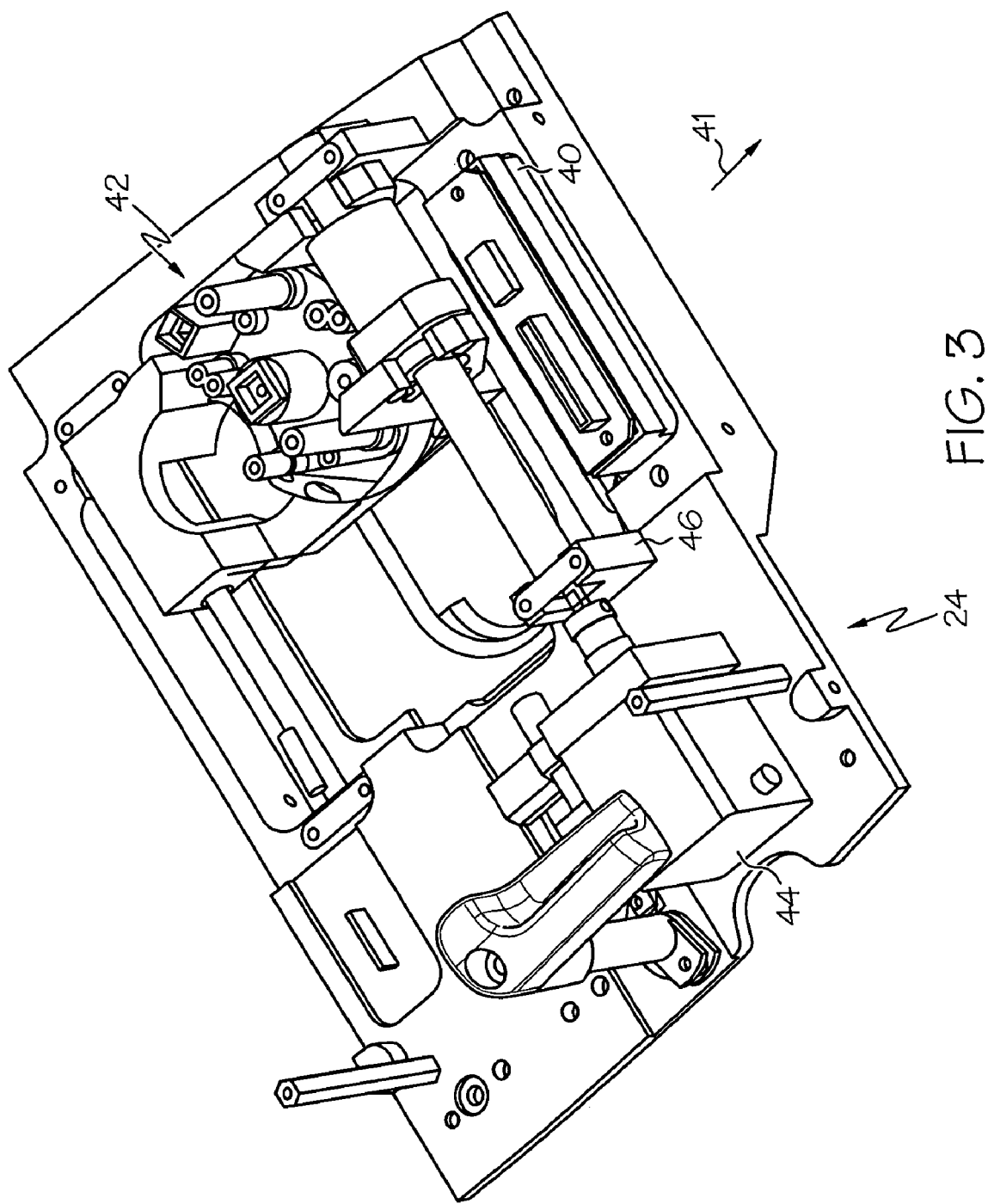
FIG. 3 shows the contents of the head of an auto-tracking spectrophotometer.

FIG. 3 shows the contents of head 24. Head 24 serves as an enclosure for various components. Various circuit boards required to operate head 24 are not shown. Arrow 41 shows the movement of the head 24 in the direction of the scan, which is referred to hereinafter as the X-direction. Head 24 includes a NCIS (non-contact image system) 40, data acquisition optics 42, and Y-step motor 44. Y-step motor 44 is connected to data acquisition optics 42 by way of y-drive mechanism 46. Information regarding the location of the color matrix is acquired by non-contact image system 40 and is used to control Y-step motor 44 in order to accurately position data acquisition optics 42 over the color matrix. NCIS 40 is spaced approximately 2½ inches from the data acquisition optics 42. Y-step motor 44 and Y-drive mechanism 46 form a positioning system.

Figure 4:
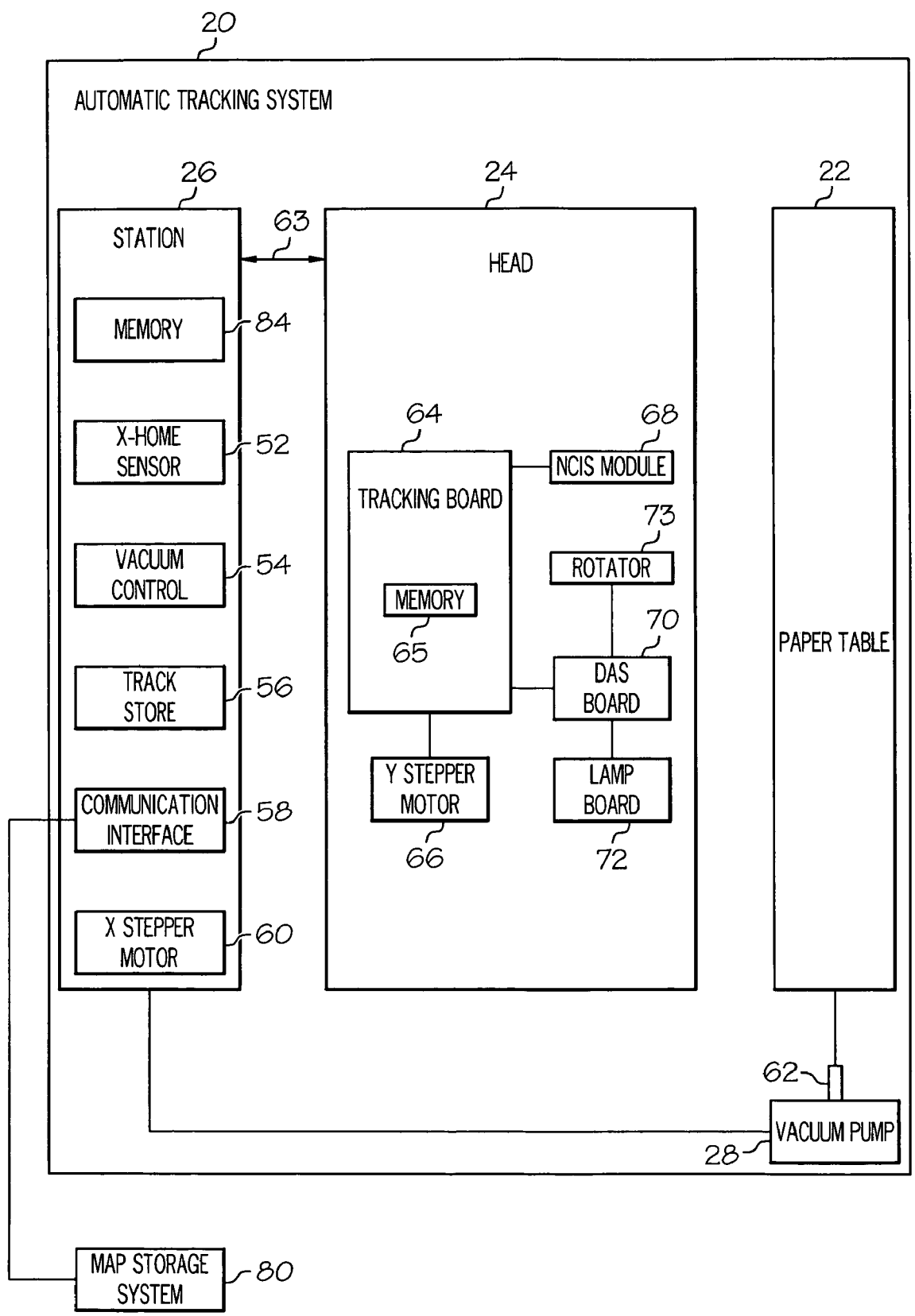
FIG. 4 shows a block diagram of an auto-tracking spectrophotometer.

FIG. 4 shows a block diagram of ATS 20. Station 26 includes x-home sensor 52, vacuum control 54, track store 56, communication interface 58, and x-stepper motor 60. X-home sensor 52 detects the x-position of head 24 whenever head 24 is docked with station 26. Vacuum control 54 is connected to vacuum pump 28. Vacuum control 54 controls vacuum inlet solenoid 62. When vacuum control 54 energizes vacuum inlet solenoid 62, a vacuum is applied to table 22. Track store 56 contains information regarding the track such as the length of the track.

Communication interface 58 provides bidrectional communication between ATS 20 and a computer or computers by way of a network. Communication interface 58 includes an Ethernet connection as well as an RS232 interface. X-stepper motor 60 controls the x-position of head 24.

Station 26 is connection to head 24 by way of interface 63 which could be an RS232 serial interface or an LVDS (Low Voltage Digital Signaling) interface. Head 24 includes tracking board 64, y-stepper motor 66, NCIS module 68, DAS (Digital Acquisition System) board 70 and lamp board 72. Tracking board 64 is connected to NCIS module 68 and DAS board 70. Station 26 could be a system for processing or storage of information from head 24. Alternatively, systems other than head station 26 could provided for the processing and storage of information.

Tracking board 64 receives information from NCIS module 68 to control the x-position of head 24 and the y-position of DAS board 70 and lamp board 72. Tracking board 64 is connected to X-stepper motor 60. Tracking board 64 provides commands to X-stepper motor 60 to move head 24. Tracking board 64 is also connected to NCIS module 68. Tracking board 64 uses the information received from NCIS module 68 to correctly position DAS board 70 and lamp board 72 in the y-direction.

DAS board 70 is connected to tracking board 64. DAS board 70 provides the color information to tracking board 64. Tracking board 64 then relays the information by way of interface 63 to station 26 and ultimately to a network or a computer. Lamp board 72 is a known device for acquiring color information from a target.

DAS board 70 could also be used to determine the thickness of the substrate, such as paper, that the image is placed upon. Additionally, the DAS board 70 or NCIS module 68 could be used to determine the speed and direction of movement of head 24.

Rotator 73 allows rotational movements of lamp board 72, the optics within lamp board 72 or head 28. Thus, rotator 73 allows the movement of the optics within DAS board 70 or DAS board 70 about an axis. For example, if a color target on an image were skewed at an angle, then rotator 73 would rotate DAS board 70 or the optics within DAS board 72 to compensate for that angle. The angle is detected by way of NCIS module 68 and tracking board 64.

Map storage system 80 stores maps of various images indicating the location of color targets on the image. For example, a page containing an image could also contain color targets at a known location with reference to the edges of the page or with respect to other reference markers on the page. Station 26 could therefore use a map of the page in order to position head 24 at or near the color targets.

Alternatively, NCIS module 68 and tracking board 64 would then precisely locate the color targets on the page for reading by DAS board 70. NCIS module 68 and tracking board 64 thus act as an alignment system. DAS board 70 could be used with NCIS module 68 and tracking board 64 to locate the color target.

Acquisition of a map or the location of the color targets could come from several sources. For example, a bar code on the image could identify the page and thereby a map of the color targets on the page. Alternatively, an operator could manually select the appropriate map. Or, a central control system could automatically communicate the map definition to the system.

The map would then be loaded from map storage system 82 into memory 84. Memory 84 is shown located within station 26. However, memory 84 could be at any convenient location. Station 26 would then move head 24 to the location of the color target based upon the map.

During a scan, an interpreter would use map information to control the location or operation of the NCIS module 68 or DAS board 70. The interpreter could then be used to insure that head 24 is properly positioned over the image. The interpreter could be a software module within tracking board 64 or station 26. Alternatively, the interpreter could be a discreet component.

As a further alternative, a bar code placed on the page could supply many data parameters to the interpreter system. For example, the bar code could include information regarding the coordinates of the color target. In that case, a bar code reader would read the bar code. A controller, which could be located in station 26, would move the head to the coordinates of the color target indicated by the bar code.

Figure 5:
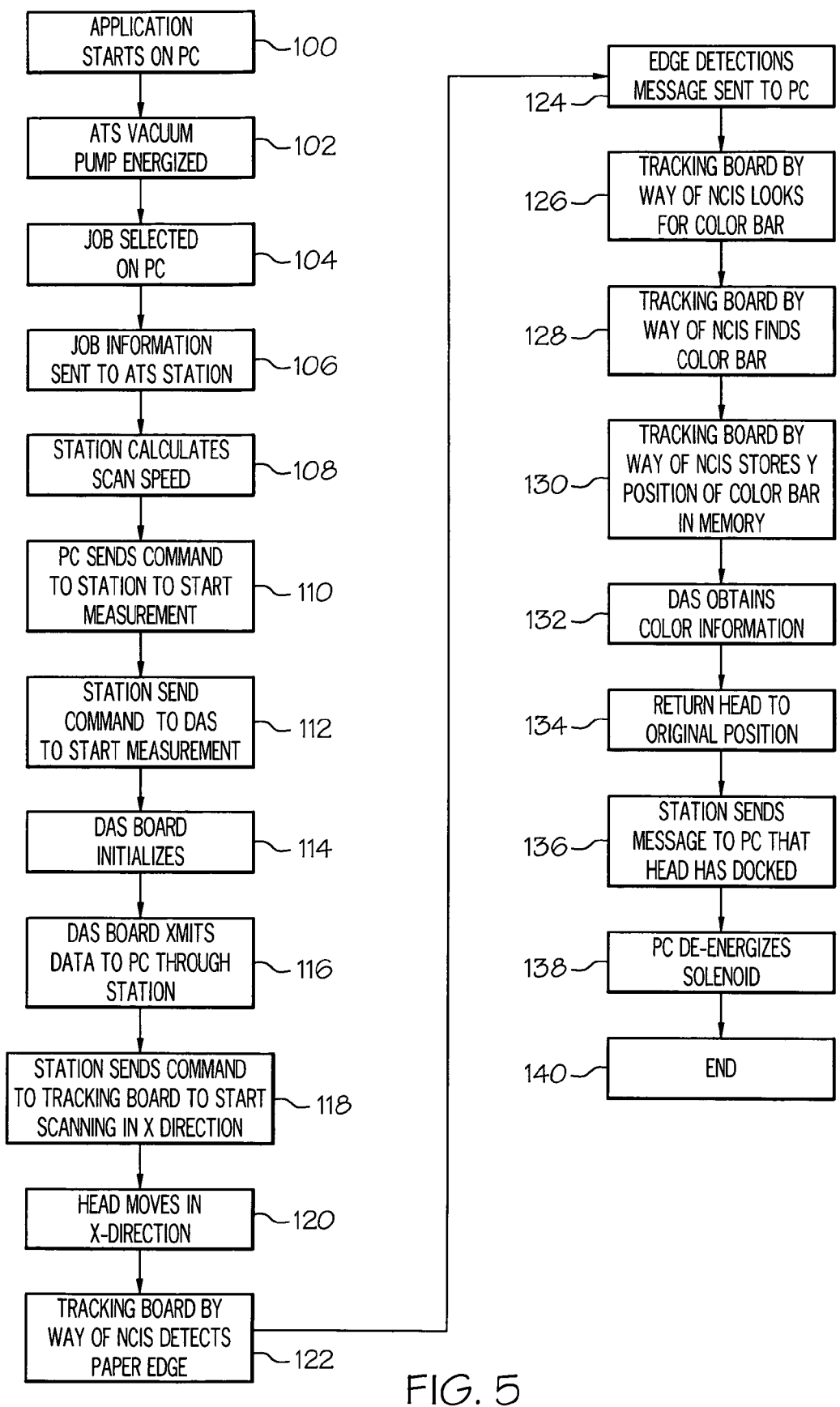
FIG. 5 is a flowchart showing the operation of an auto-tracking spectrophotometer.

FIG. 5 is a flowchart showing the operation of ATS 20. A color calibration application starts on a computer connected to ATS 20. Step 100. When ATS 20 receives a signal from the computer that an application has started, ATS 20 energizes vacuum pump 28. Step 102. In this way, a vacuum will be immediately accessible at table 22. After a job is selected on the computer (Step 104), the job information is sent to station 26. Step 106. The job information could include data regarding the size of the color matrix such as height, width of individual color patches within the color matrix, number of colors.

From the job information, station 26 calculates the optimal speed for movement of head 24 in the x-direction. Step 108. The PC then sends a command to station 26 to start the color measurement. Step 110. Station 26 then sends a command to DAS board 70 to begin measurement. Step 112. DAS board 70 then initializes itself by performing such tasks as, spinning the color wheels, energizing the lamp, and energizing the sensors. Step 114. DAS board 70 then begins sending information to the computer. Step 116. When communication between the DAS board 70 and the computer is confirmed, station 26 sends a command to tracking board 64 to begin scanning in the x-direction. Step 118. Tracking board 64 then sends a command to x-stepper motor 60 to move head 24 in the x-direction. Step 120.

Tracking board 64, by way of NCIS module 68, then begins to look for the paper edge. Step 122. When a paper edge is detected by tracking board 64, tracking board 64 sends a message to the computer that a paper edge has been found and also sends to the computer the X/Y-location of the paper edges. Step 124. After the edge is found, tracking board 64 by way of NCIS module 68 begins to search for the color matrix. Step 126. When the color matrix is found (step 128) the tracking board 64 stores the x/Y-location of the start of the color matrix in memory. Step 130.

Tracking board 64 controls x-stepper motor 60 and maintains a counter indicative of the x-position of head 24. DAS board 70 then collects color information from the color matrix. Step 132.

Figure 6:
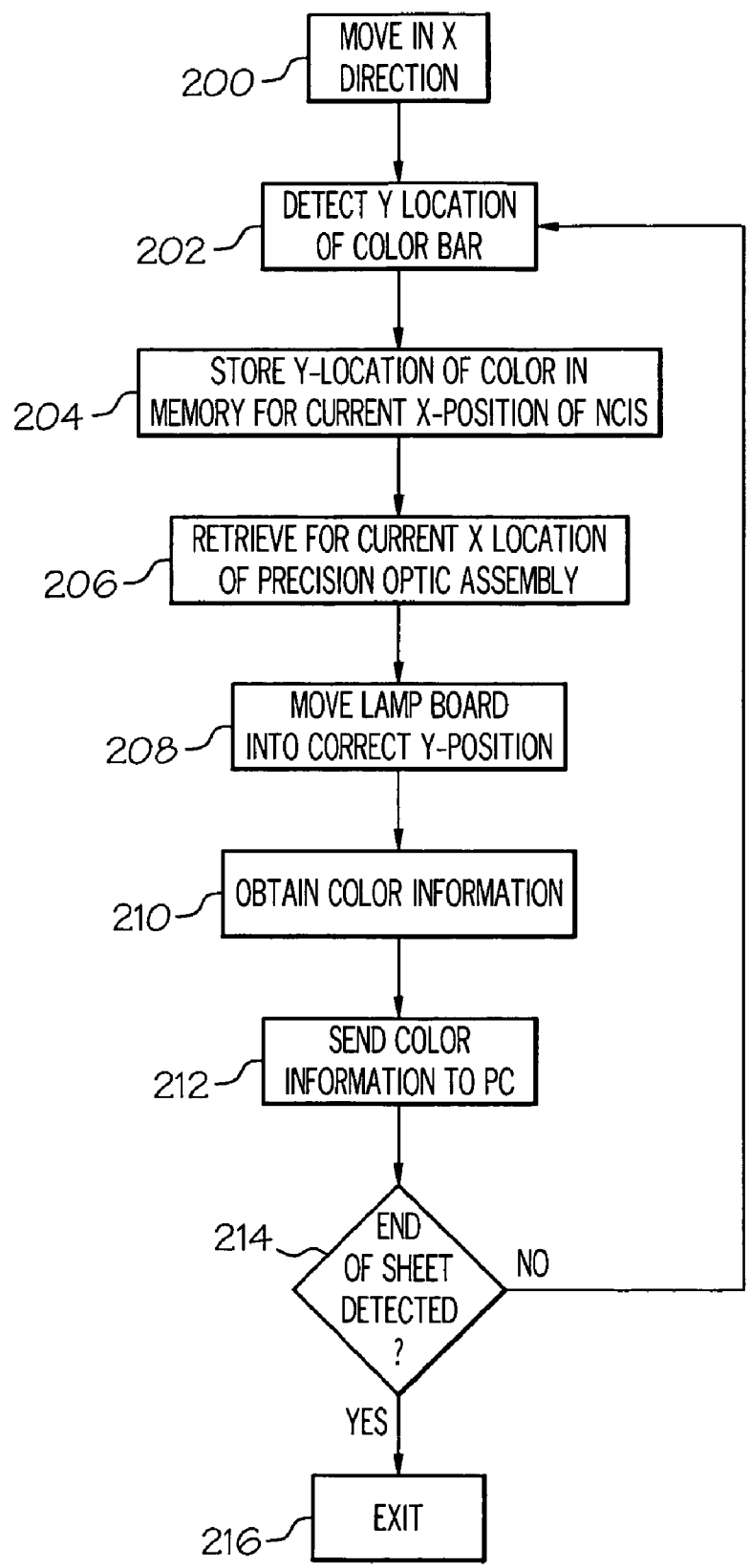
FIG. 6 is a flowchart indicating shows how the color information is collected from color matrix by an auto-tracking spectrophotometer.

FIG. 6 is a flow chart indicating shows how the color information is collected from color matrix 132. Tracking board 64 sends a command to X-stepper motor 60 to move head 24 in the x-direction. Step 200. Tracking board 64 stores the x-location of the head 24 in memory 65. Tracking board 64 by way of the NCIS module 68 detects the Y-location of the color matrix. Step 202. It stores the Y-location in memory 65. Step 204. Because NCIS module 68 is located approximately 2½ inches in advance of lamp board 72, tracking board 64 uses previously stored data regarding location of the color matrix to control the y-position of lamp board 72 with stepper motor 66.

Tracking board 64 retrieves the y-position of the color matrix for the current x-position of the lamp board 72 from memory 65. Step 206. Tracking board 64 then moves lamp board 72 to the current y-position. Step 208. Color information is then read from the color matrix. Step 210. The color information is then sent to the computer. Step 212.

At the same time NCIS module 68, is searching for the edge of the paper. Step 214. If the edge is detected, then the reading of the color matrix ends. Otherwise, the process repeats.

Returning to FIG. 5, after all color information has been collected, 24 head is returned to its original position. Step 134. When head 24 is docked with station 26, ATS 20 sends a message to the computer that head 24 is docked. Step 136. The solenoid is de-energized. Step 138. The color reading is then completed. Step 140.

Color patches are often aligned sequentially on the paper or substrate. Additionally, a color patch may be a solid color or a gradient of the same color. By comparing color threshold information within the patch, the location of either the DAS board 70 or NCIS module 68 relative to the color patch could be determined.

For example, if color patches of different colors were juxtaposed, the color measurement at the center of each color patch would be significantly different than a measurement near the edge of the color patch. Similarly, if a color patch was a gradient of a color, a color measurement at one edge of the color patch would be significantly different than that at the other edge of the color patch. Thus, by detecting the differences in color measurements, the location of DAS board 70 or NCIS module 68 with reference to a particular patch can be determined.

The above description is of the preferred embodiment. Various alterations and changes can be made without departing from the spirit and broader aspects of the invention as defined in the appended claims, which are to be interpreted in accordance with the principles of patent law including the doctrine of equivalents. Any references to claim elements in the singular, for example, using the articles "a," "an," "the," or "said," is not to be construed as limiting the element to the singular.

The embodiments of the invention in which an exclusive property or privilege is claimed are defined as follows:

1. A measurement head for facilitating detection of a visual characteristic of a target on a substrate, the measurement head comprising:
   a. a look-ahead sensor associated with a target tracking system; and
   b. a data acquisition unit;
   wherein the measurement head is movable relative to a substrate, thereby defining a measurement path for the measurement head, the look-ahead sensor preceding the data acquisition unit along the measurement path such that the look-ahead sensor anticipates a scan path for a component of the data acquisition unit relative to the substrate;
   wherein the look-ahead sensor and the target tracking system are adapted to determine a spatial characteristic of a target on the substrate when the target is at least partially within a field of view of the look-ahead sensor;
   wherein at least one of: (i) the scan path for the component of the data acquisition unit, and (ii) the orientation of the component of the data acquisition unit is adjusted, relative to the substrate, based on the determined spatial characteristic of the target, such that, as the measurement head advances along the measurement path, the data acquisition unit is better configured to detect a visual characteristic of the target.

2. The measurement head of claim 1, wherein the measurement head is adapted for use in connection with an auto-tracking spectrophotometer.

3. The measurement head of claim 1, further comprising an enclosure, wherein the look-ahead sensor and the data acquisition unit are disposed within the enclosure.

4. The measurement head of claim 1, further comprising an internal positioning system for the data acquisition unit, wherein the internal positioning system is adapted to adjust at least one of: (i) the location, and (ii) the orientation of the component of the data acquisition unit within the measurement head.

5. The measurement head of claim 4, wherein the internal positioning system provides translational means for translating the component of the data acquisition unit in at least a first direction.

6. The measurement head of claim 4, wherein the internal positioning system provides rotational means for rotating the component of the data acquisition means about at least a first axis.

7. The measurement head of claim 1, wherein the field of view for the look-ahead sensor is greater than a field of view of the data acquisition unit.

8. The measurement head of claim 1, wherein the measurement head is associated with a mapping storage system including information indicating an expected location of the target, wherein the measurement head is moveable proximate to the target based on the expected location of the target.

9. A method for facilitating detection of a visual characteristic of a target on a substrate, the method comprising:
   a. providing a measurement head including a look-ahead sensor associated with a target tracking system and a data acquisition unit;
   b. moving the measurement head relative to a substrate, thereby defining a measurement path for the measurement head, the look-ahead sensor preceding the data acquisition unit along the measurement path such that the look-ahead sensor anticipates a scan path for a component of the data acquisition unit relative to the substrate;
   c. using the look-ahead sensor and the target tracking system to determine a spatial characteristic of a target on the substrate when the target is at least partially within a field of view of the look-ahead sensor;
   d. adjusting, relative to the substrate, at least one of: (i) the scan path for the component of the data acquisition unit, and (ii) the orientation of the component of the data acquisition unit based on the determined spatial characteristic of the target, such that, as the measurement head advances along the measurement path, the data acquisition unit is better configured to detect a visual characteristic of the target.

10. The method of claim 9, wherein the target includes a first color threshold and a second color threshold, wherein the spatial characteristic of the target is determined based on the first and second color thresholds.

11. The method of claim 9, wherein the target is a color strip and wherein the spatial characteristic of the color strip is at least one of: (i) a center line for the color strip, (ii) an edge of the color strip, and (iii) and an angle of the color strip.

12. The method of claim 9, wherein the adjustment of the at least one of: (i) the scan path for the component of the data acquisition unit, and (ii) the orientation of the component of the data acquisition unit, includes using an internal positioning system for the data acquisition unit to adjust at least one of: (i) the location, and (ii) the orientation of the component of the data acquisition unit within the measurement head.

13. The method of claim 12, wherein the internal positioning system provides translational means for translating the component of the data acquisition unit in at least a first direction.

14. The method of claim 12, wherein the internal positioning system provides rotational means for rotating the component of the data acquisition means about at least a first axis.

15. The method of claim 9, wherein moving the measurement head relative to a substrate includes using a mapping storage system to move the measurement head proximate to an expected location of the target.

16. An auto-tracking spectrophotometer for facilitating detection of a visual characteristic of a target on a substrate, the spectrophotometer comprising:
   a. a measurement head including a look-ahead sensor and a data acquisition unit;
   b. an external positioning system for the measurement head, whereby the measurement head is movable relative to a substrate, thereby defining a measurement path for the measurement head, the look-ahead sensor preceding the data acquisition unit along the measurement path such that the look-ahead sensor anticipates a scan path for a component of the data acquisition unit relative to the substrate;
   c. a target tracking system associated with the look-ahead sensor, wherein the look-ahead sensor and the target tracking system are adapted to determine a spatial characteristic of a target on the substrate when the target is at least partially within a field of view of the look-ahead sensor;
   wherein at least one of: (i) the scan path for the component of the data acquisition unit, and (ii) the orientation of the component of the data acquisition unit is adjusted, relative to the substrate, based on the determined spatial characteristic of the target, such that, as the measurement head advances along the measurement path, the data acquisition unit is better configured to detect a visual characteristic of the target.

17. The spectrophotometer of claim 16, further comprising a substrate holding surface including means for holding the substrate relative to the surface.

18. The spectrophotometer of claim 16, further comprising an internal positioning system for the data acquisition unit, wherein the internal positioning system is adapted to adjust at least one of: (i) the location, and (ii) the orientation of the component of the data acquisition unit within the measurement head.

19. The spectrophotometer of claim 18, wherein the internal positioning system provides translational means for translating the component of the data acquisition unit in at least a first direction.

20. The spectrophotometer of claim 18, wherein the internal positioning system provides rotational means for rotating the component of the data acquisition means about at least a first axis.

21. The spectrophotometer of claim 18, wherein the external positioning system enables movement of the measurement head along a first axis and wherein the internal positioning system enables movement of the component of the data acquisition unit within the measurement head along a second axis, wherein the first and second axes are parallel to a surface of the substrate.

22. The spectrophotometer of claim 21, wherein the first and second axes are perpendicular to one another.

23. The spectrophotometer of claim 18, further comprising a mapping storage system associated with the external positioning system, wherein the mapping storage system includes information indicating an expected location of the target, wherein the external positioning system is adapted to move the measurement head proximate to the target based on the expected location of the target.

24. A measurement head for facilitating detection of a visual characteristic of a target on a substrate, the measurement head being movable relative to the substrate so as to define a measurement path thereof, the measurement head comprising:
   a. a look-ahead sensor, configured to monitor the measurement path of the measurement head, wherein the look-ahead sensor is associated with a positional tracking system adapted to determine a positional characteristic of the target when the target is at least partially within a field of view of the look-ahead sensor, and
   b. a data acquisition unit configured to detect a visual characteristic of the target, wherein positions of one or more components of the data acquisition unit relative to the substrate are adjusted based on the determined positional characteristic of the target, such that the target is better located within a field of view of the data acquisition unit as the measuring head advances along the measurement path.

25. A measurement head for facilitating detection of a visual characteristic of a target on a substrate, the measurement head being movable relative to the substrate so as to define a measurement path thereof, the measurement head comprising:
   a. a look-ahead sensor, configured to monitor the measurement path of the measurement head, wherein the look-ahead sensor is associated with an angular tracking system adapted to determine an angular characteristic of the target when the target is within a field of view of the look-ahead sensor, and
   b. a data acquisition unit configured to detect a visual characteristic of the target, wherein orientations of one or more components of the data acquisition unit relative to the substrate are adjusted based on the determined angular characteristic of the target, such that the target is better aligned within a field of view of the data acquisition unit as the measuring head advances along the measurement path.

* * * * *